(12) United States Patent
Wallenstein

(10) Patent No.: US 9,186,182 B2
(45) Date of Patent: Nov. 17, 2015

(54) SPINAL STABILIZATION SYSTEM

(71) Applicant: K2M, Inc., Leesburg, VA (US)

(72) Inventor: Todd Wallenstein, Ashburn, VA (US)

(73) Assignee: K2M, Inc., Leesburg, VA (US)

( * ) Notice: Subject to any disclaimer, the term of this patent is extended or adjusted under 35 U.S.C. 154(b) by 193 days.

(21) Appl. No.: 13/675,123

(22) Filed: Nov. 13, 2012

(65) Prior Publication Data
US 2014/0135842 A1 May 15, 2014

(51) Int. Cl.
*A61B 17/70* (2006.01)
*A61B 17/88* (2006.01)

(52) U.S. Cl.
CPC ........... *A61B 17/701* (2013.01); *A61B 17/7032* (2013.01); *A61B 17/8863* (2013.01)

(58) Field of Classification Search
CPC ........... A61B 17/7002; A61B 17/7011; A61B 17/7032; A61B 17/7059
USPC ......... 606/246, 264–270, 279, 301, 305, 308; 411/337
See application file for complete search history.

(56) References Cited

U.S. PATENT DOCUMENTS

| 5,113,685 A | 5/1992 | Asher et al. |
|---|---|---|
| 5,217,497 A | 6/1993 | Mehdian |
| 5,261,912 A | 11/1993 | Frigg |
| 5,658,286 A | 8/1997 | Sava |
| 5,667,508 A | 9/1997 | Errico et al. |
| 5,899,904 A | 5/1999 | Errico et al. |
| 5,910,142 A | 6/1999 | Tatar |
| 5,947,969 A | 9/1999 | Errico et al. |
| 6,102,912 A | 8/2000 | Cazin et al. |
| 6,451,021 B1 | 9/2002 | Ralph et al. |
| 6,482,207 B1 | 11/2002 | Errico |
| 6,540,749 B2 | 4/2003 | Schafer et al. |
| 6,582,434 B2 | 6/2003 | Kawakami et al. |
| 6,644,087 B1 | 11/2003 | Ralph et al. |
| 7,503,918 B2 | 3/2009 | Baccelli et al. |
| 7,520,879 B2 | 4/2009 | Justis et al. |
| 7,563,274 B2 | 7/2009 | Justis et al. |
| 7,569,061 B2 | 8/2009 | Colleran |
| 7,588,575 B2 | 9/2009 | Colleran et al. |
| 7,588,588 B2 | 9/2009 | Spitler et al. |
| 7,604,653 B2 | 10/2009 | Kitchen |
| 7,618,442 B2 | 11/2009 | Spitler et al. |
| 7,766,942 B2 | 8/2010 | Patterson et al. |
| 7,931,676 B2 | 4/2011 | Veldman et al. |
| 2002/0161368 A1 | 10/2002 | Foley et al. |
| 2005/0065515 A1 | 3/2005 | Jahng |
| 2005/0096653 A1* | 5/2005 | Doubler et al. ................. 606/61 |
| 2008/0027432 A1 | 1/2008 | Strauss et al. |
| 2008/0086130 A1* | 4/2008 | Lake et al. ...................... 606/61 |

(Continued)

*Primary Examiner* — Pedro Philogene
*Assistant Examiner* — David Comstock
(74) *Attorney, Agent, or Firm* — Carter, DeLuca, Farrell & Schmidt, LLP

(57) ABSTRACT

A spinal stabilization system includes a connecting rod and a bone screw. The connecting rod includes an elongate rounded section, an elongate head portion, and a neck portion connecting the elongate rounded section with the elongate head portion. The bone screw includes a head portion defining a slot, a shank extending longitudinally from the head portion, and a cap. The slot includes a leading end portion configured to receive the elongate rounded section of the connecting rod and a trailing end portion defining a planar surface. The cap is configured to enclose the planar surface of the trailing end portion of the slot and secure the connecting rod in the slot to the bone screw.

17 Claims, 9 Drawing Sheets

(56) References Cited

U.S. PATENT DOCUMENTS

2008/0262546 A1 10/2008 Calvosa et al.
2009/0018593 A1 1/2009 Barrus et al.
2011/0087298 A1 4/2011 Jones
2011/0190823 A1 8/2011 Bergeron et al.

* cited by examiner

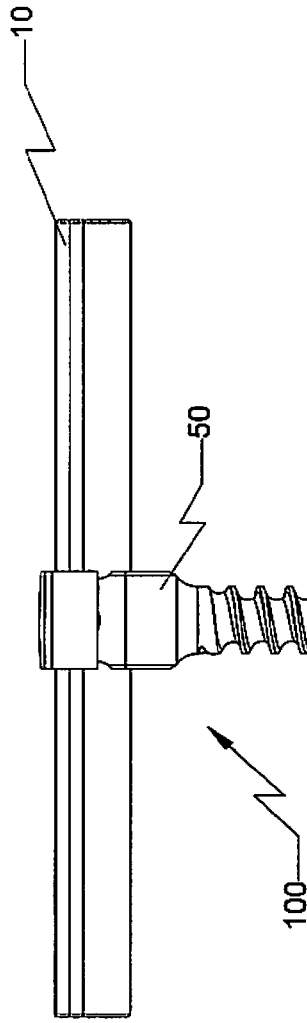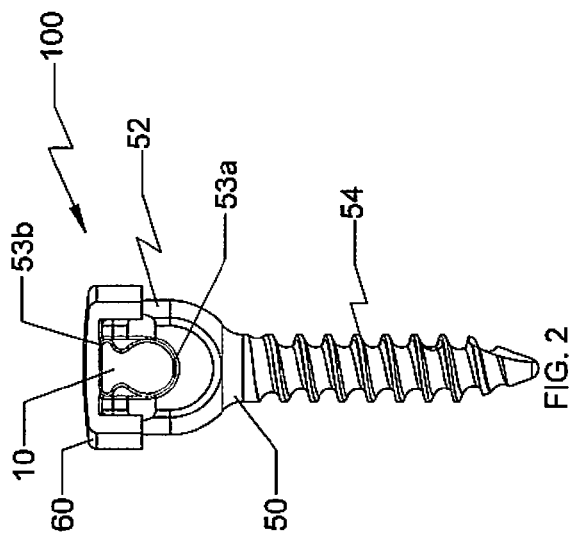

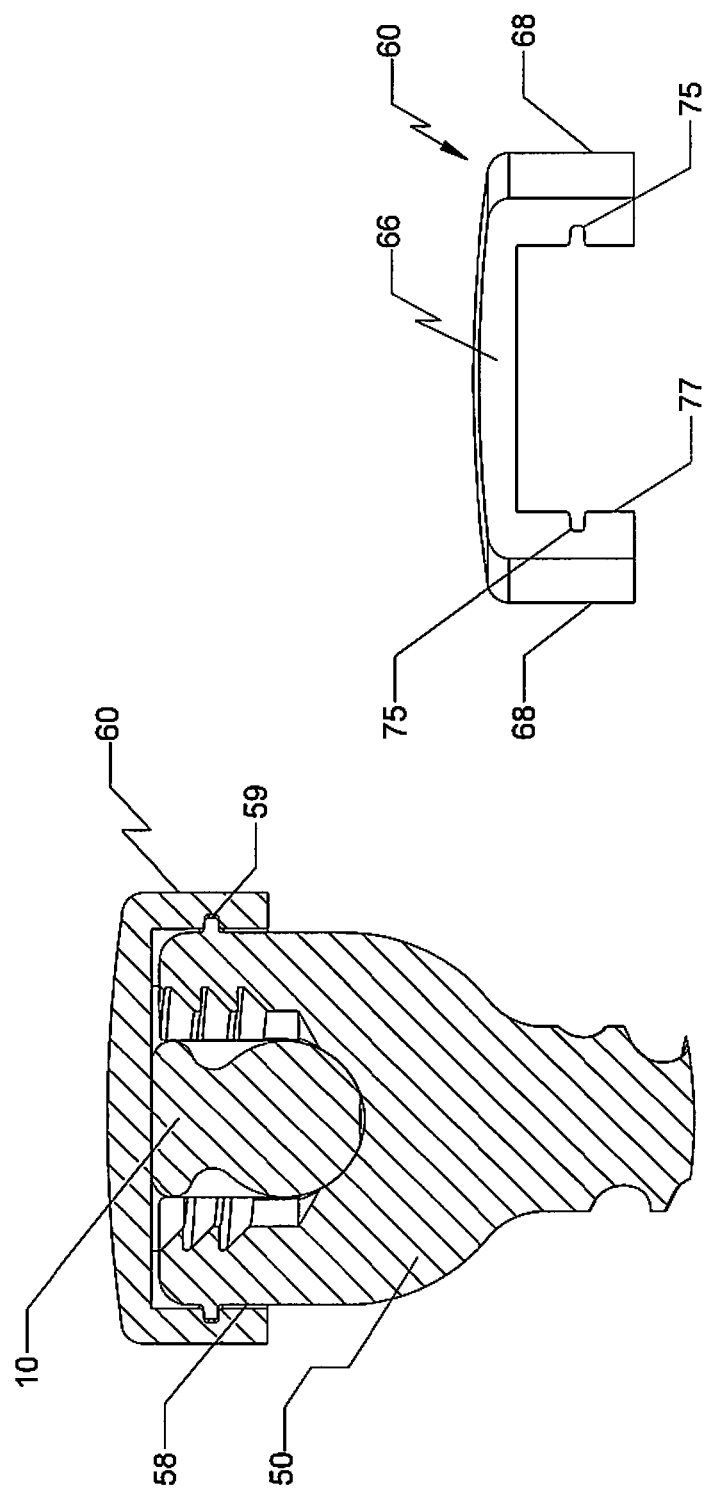

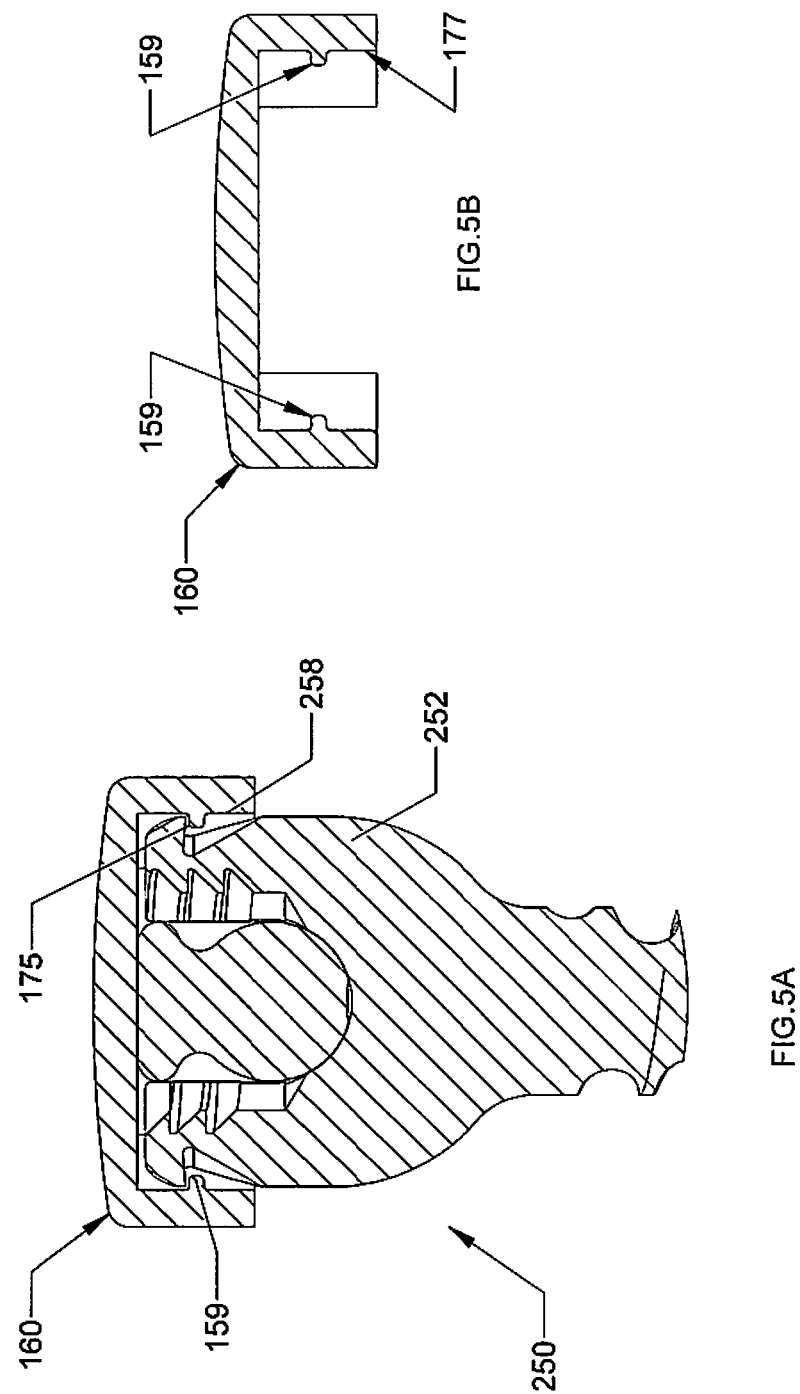

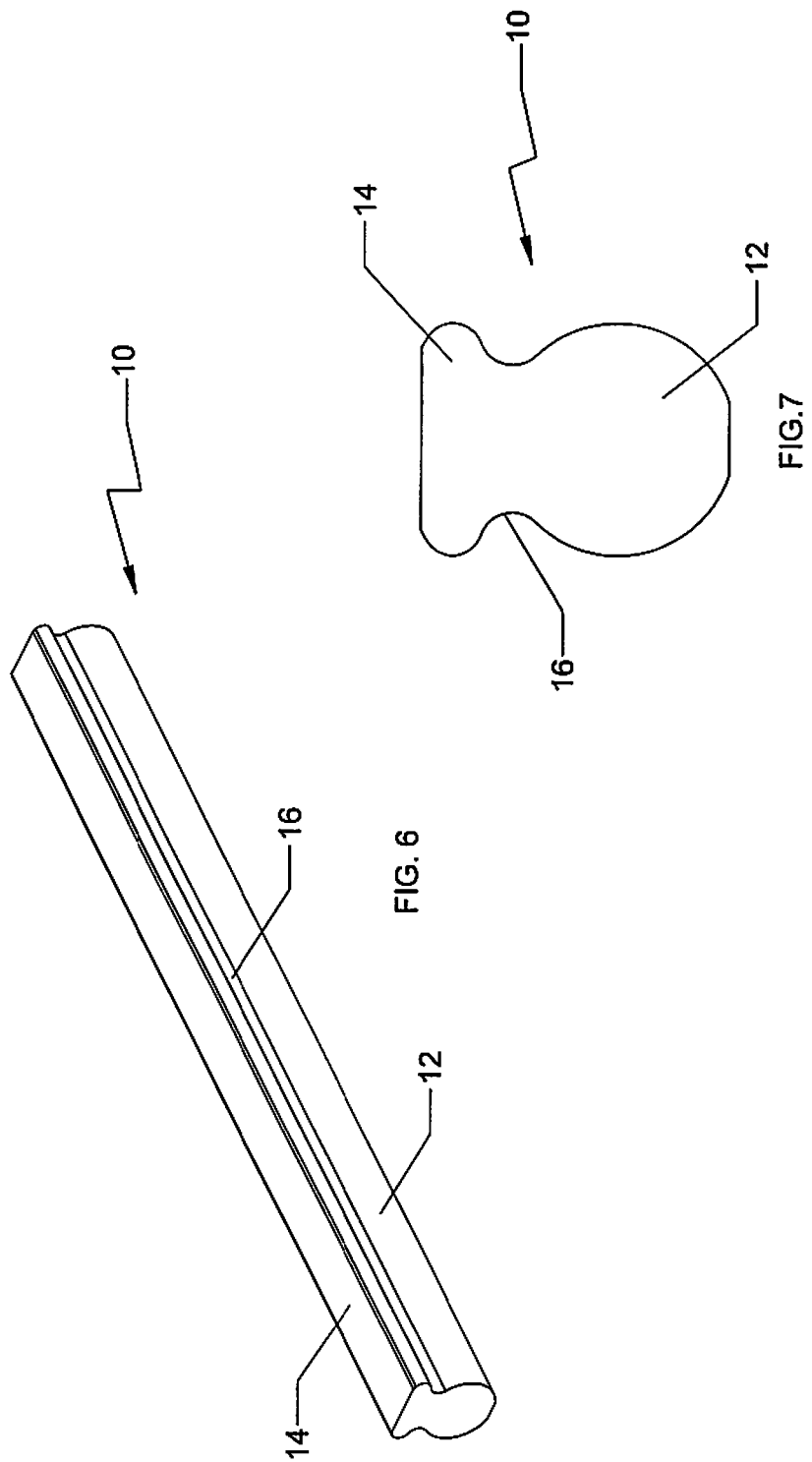

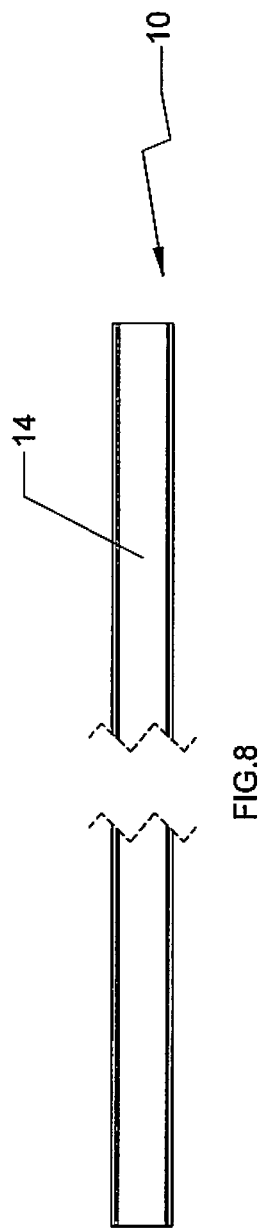
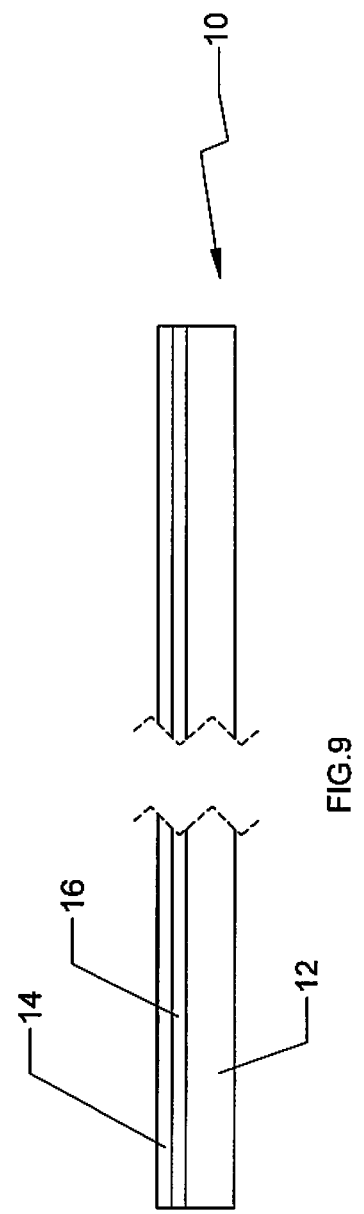

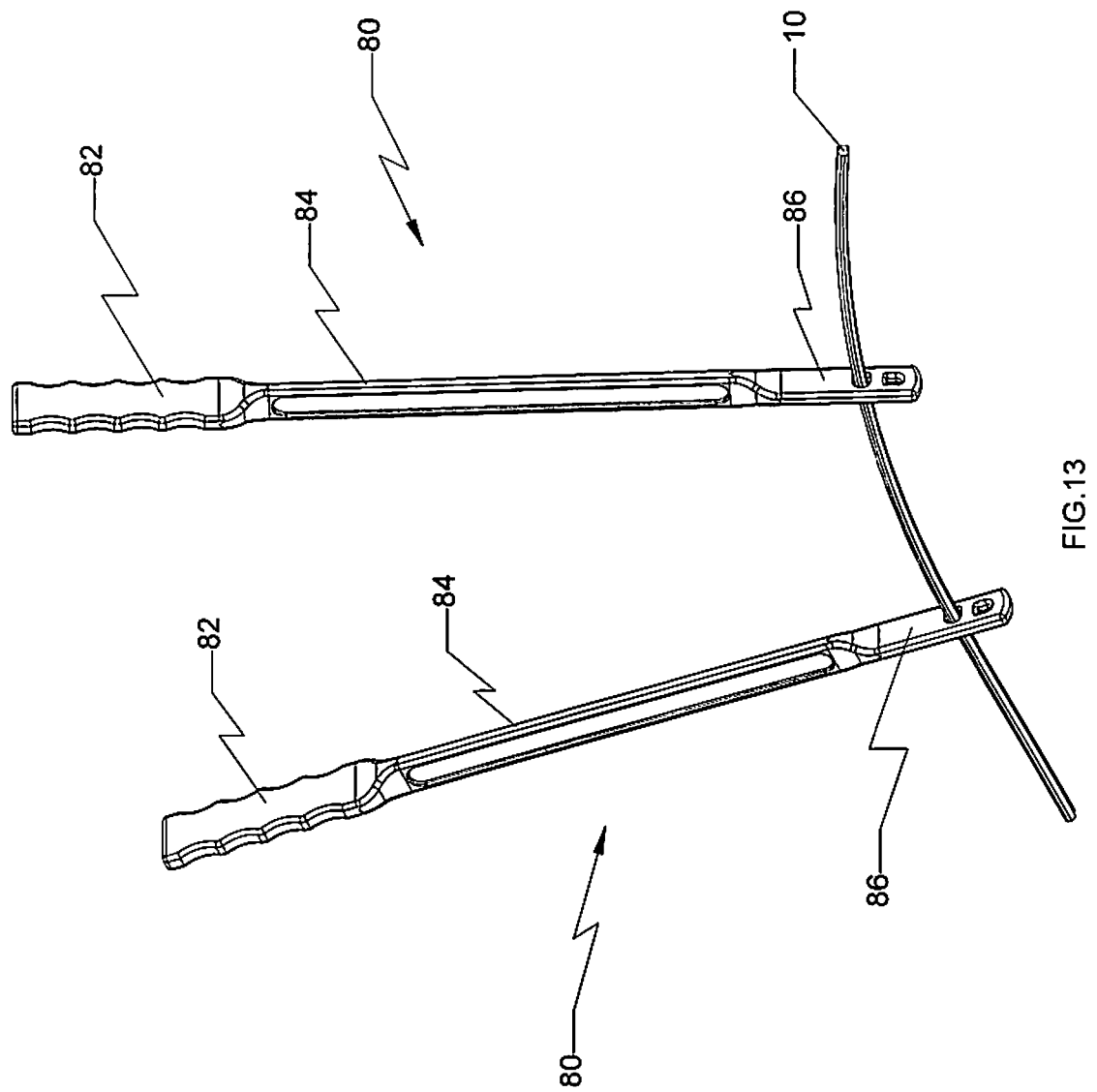

SPINAL STABILIZATION SYSTEM

BACKGROUND

1. Technical Field

The present disclosure relates to orthopedic surgical devices and, more particularly, to a spinal stabilization system.

2. Background of Related Art

The spinal column is a complex system of bones and connective tissues that provide support for the human body and protection for the spinal cord and nerves. The adult spine is comprised of an upper and lower portion. The upper portion contains twenty-four discrete bones, which are subdivided into three areas including seven cervical vertebrae, twelve thoracic vertebrae, and five lumbar vertebrae. The lower portion is comprised of the sacral and coccygeal bones. The cylindrical shaped bones, called vertebral bodies, progressively increase in size from the upper portion downwards to the lower portion.

An intervertebral disc along with two posterior facet joints cushion and dampen the various translational and rotational forces exerted upon the spinal column. The intervertebral disc is a spacer located between two vertebral bodies. The facets provide stability to the posterior portion of adjacent vertebrae. The spinal cord is housed in the canal of the vertebral bodies. It is protected posteriorly by the lamina. The lamina is a curved surface with three main protrusions. Two transverse processes extend laterally from the lamina, while the spinous process extends caudally and posteriorly. The vertebral bodies and lamina are connected by a bone bridge called the pedicle.

The spine is a flexible structure capable of a large range of motion. There are various disorders, diseases and types of injury, which restrict the range of motion of the spine or interfere with important elements of the nervous system. The problems include, for example, scoliosis, kyphosis, excessive lordosis, spondylolisthesis, slipped or ruptured discs, degenerative disc disease, vertebral body fracture, and tumors. Persons suffering from any of the above conditions typically experience extreme or debilitating pain and often times diminished nerve Spinal fixation apparatuses are widely employed in surgical processes for correcting spinal injuries and diseases. When the disc has degenerated to the point of requiring removal, there are a variety of interbody implants that are utilized to take the place of the disc. These include interbody spacers, metal cages and cadaver and human bone implants. In order to facilitate stabilizing the spine and keeping the interbody in position, other implants are commonly employed, such as bone screws and connecting rods.

In the case of set screw type bone screws, torsional force is required to threadably insert the set screw into the head of the bone screw to secure the connecting rod to the bone screw. Alternatively, in the case of a taper lock type bone screw, additional tools are needed to move an outer housing of the taper lock type bone screw relative to an inner housing of the taper lock screw to secure the connecting rod to the bone screw.

Therefore, a need exists for a simple and effective screw and rod construct that enables surgeons to easily and safely secure a connecting rod to bone screws during a surgical procedure.

SUMMARY

In accordance with an embodiment of the present disclosure, there is provided a spinal stabilization system including a connecting rod and a bone screw. The connecting rod includes an elongate rounded section, an elongate head portion, and a neck portion connecting the elongate rounded section with the elongate head portion. The bone screw includes a head portion defining a slot, a shank extending longitudinally from the head portion, and a cap. The slot includes a leading end portion configured to receive the elongate rounded section of the connecting rod and a trailing end portion defining a planar surface, wherein the cap is configured to enclose the planar surface of the trailing end portion of the slot and secure the connecting rod in the slot to the bone screw.

In an embodiment, the elongate head portion of the connecting rod may be substantially flush with the planar surface of the trailing end portion of the slot when the connecting rod is secured in the slot. In addition, the leading end of the slot may have an arcuate configuration dimensioned to accommodate the contour of the elongate rounded section of the connecting rod.

In another embodiment, the cap may include a cover and a pair of opposing arms extending from the cover and defining a gap therebetween. The gap may be smaller than an outer diameter of the head portion of the bone screw. The cover of the cap may be in planar contact with the elongate head portion of the connecting rod when the connecting rod is secured in the slot.

In yet another embodiment, the head portion of the bone screw may include a pair of radially opposing walls defining the slot therebetween. The walls may securely engage the respective arms of the cap. The pair of radially opposing walls may be aligned with the pair of opposing arms of the cap when the cap is secured with the head portion. The pair of walls may each include an engaging portion configured to engage an inner surface of the respective arms of the cap. In particular, each arm of the cap defines a recess formed therein. The recess may be configured and dimensioned to engage a protrusion member extending radially outward from the engaging portion. Alternatively, the engaging portion may define a recess configured and dimensioned to securely engage a protrusion formed in the arm of the cap. The protrusion may extend radially inward from the inner surface of the arm of the cap.

In still another embodiment, the neck portion of the connecting rod may be narrower than the elongate rounded section of the connecting rod. The width of the elongate head portion of the connecting rod may be substantially identical to the radius of the slot.

In yet another embodiment, the cap may be releasably attached to the head portion of the bone screw. The cap may be attached to the head portion of the bone screw by a friction fit or a snap fit. The pair of walls of the head portion of the bone screw may include internal threads. The shank of the bone screw may include threads. The cap and the head portion may be made of the same material. In particular, the cap may be made of titanium or titanium alloy.

In accordance with yet another embodiment of the present disclosure, there is provided a spinal stabilization including a connecting rod and a bone screw. The connecting rod includes an elongate rounded section, an elongate head portion, and a neck portion connecting the elongate rounded section with the elongate head portion. The bone screw includes a head portion defining a slot, a shank extending longitudinally from the head portion, and a cap configured to secure the connecting rod in the slot. In particular, the head portion includes an engaging portion configured to secure the cap thereon, wherein the cap defines a recess formed therein. The recess is configured and dimensioned to engage a protrusion member extending radially outward from the engaging portion.

In accordance with still yet another embodiment of the present disclosure, there is provided a spinal stabilization system including a connecting rod and a bone screw. The connecting rod includes an elongate rounded section, an elongate head portion, and a neck portion connecting the elongate rounded section with the elongate head portion. The bone screw includes a head portion defining a slot, a shank extending longitudinally from the head portion, and a cap configured to secure the connecting rod in the slot. In particular, the head portion includes an engaging portion configured to secure the cap thereon, wherein the cap includes a protrusion extending radially inward. The protrusion is configured and dimensioned to engage a recess defined in the engaging portion.

BRIEF DESCRIPTION OF THE DRAWINGS

The foregoing and other features of the present disclosure will become apparent to one skilled in the art to which the present disclosure relates upon consideration of the following description of the disclosure with reference to the accompanying drawings, wherein:

FIG. 1 is a side view of a spinal stabilization system in accordance with an embodiment of the present disclosure;

FIG. 2 is an end view of the spinal stabilization system of FIG. 1;

FIG. 4A is a partial, cross-sectional view of the spinal stabilization system of FIG. 2 illustrating engagement of a cap on a head portion of a bone screw;

FIG. 4B is a cross-sectional view of the cap of FIG. 4A;

FIG. 5A is a partial, cross-sectional view of a spinal stabilization system in accordance with another embodiment of the present disclosure;

FIG. 5B is a cross-sectional view of a cap of the spinal stabilization system of FIG. 5A;

FIG. 6 is a perspective view of a connecting rod of the spinal stabilization system of FIG. 1;

FIG. 7 is an end view of the connecting rod of FIG. 6;

FIG. 8 is a top view of the connecting rod of FIG. 6;

FIG. 9 is a side view of the connecting rod of FIG. 6;

FIG. 13 is a perspective view of the pair of rod bender devices of FIG. 10 having the connecting rod of FIG. 6 inserted therethrough in a different orientation.

DETAILED DESCRIPTION OF EMBODIMENTS

Figure 3:
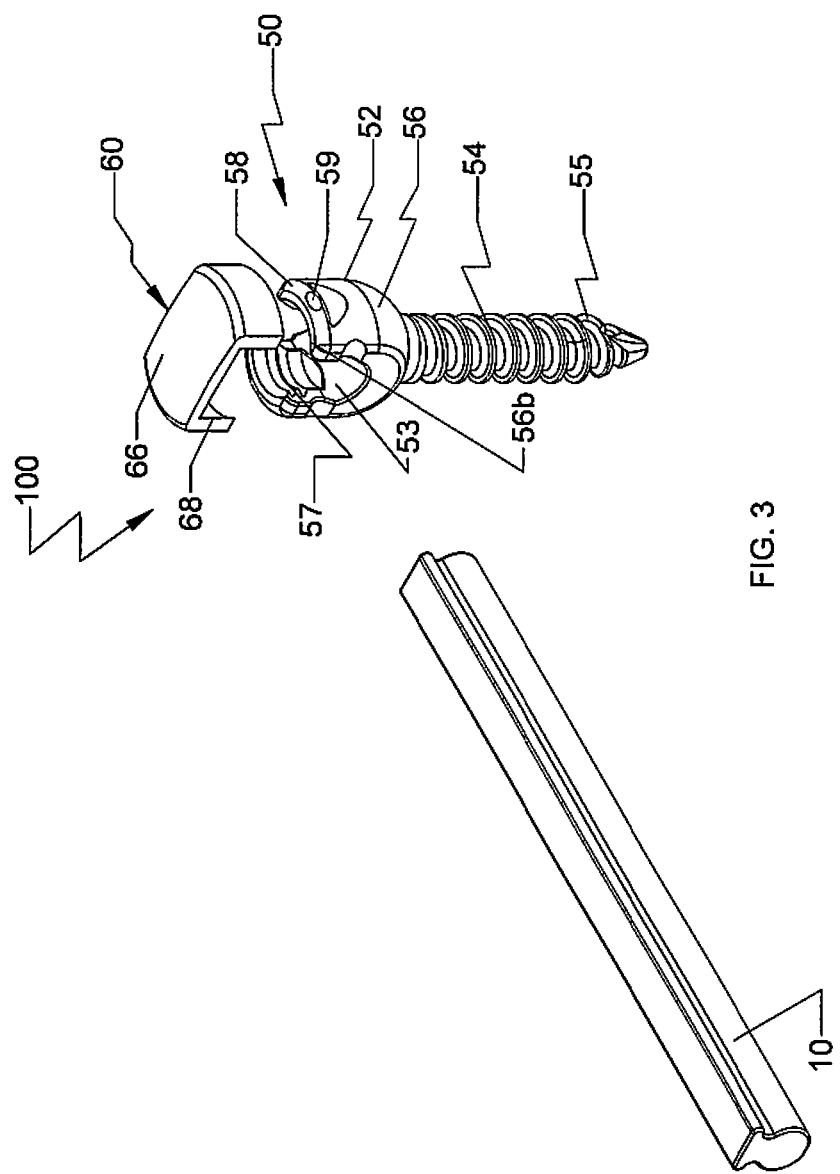
FIG. 3 is an exploded perspective view of the spinal stabilization system of FIG. 1 with parts separated.

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In addition, the term "cephalad" is used in this application to indicate a direction toward a patient's head, while the term "caudad" indicates a direction toward the patient's feet. Further still, for the purposes of this application, the term "medial" indicates a direction toward the middle of the body of the patient, while the term "lateral" indicates a direction toward a side of the body of the patient, i.e., away from the middle of the body of the patient. The term "posterior" indicates a direction toward the patient's back, while the term "anterior" indicates a direction toward the patient's front. In the following description, well-known functions or constructions are not described in detail to avoid obscuring the present disclosure in unnecessary detail.

With reference to FIGS. 1-3, an embodiment of the present disclosure is shown generally as a spinal stabilization system 100. Spinal stabilization system 100 includes at least one bone screw 50 and a connecting rod 10. Connecting rod 10 is configured and dimensioned to be selectively and releasably secured to bone screw 50. Connecting rod 10 is defined by an elongate body of a particular length. The elongate body is made of a biocompatible material such as Titanium (Ti-CP) and its alloys (e.g., Ti-6Al-4V), Cobalt-Chrome Alloy (CoCr), or Stainless Steel (SS).

With reference to FIGS. 6 and 7, the elongate body of connecting rod 10 includes an elongate rounded section 12 having a substantially circular cross-section, an elongate head portion 14, and a neck portion 16 that connects and transitions elongate rounded section 12 into elongate head portion 14, thereby providing reduced stress concentration along the elongate body of connecting rod 10. Neck portion 16 may define a pair of concave sides joining elongate head portion 14 to elongate rounded section 12. The elongate body of connecting rod 10 may be monolithically formed as a unitary construct. For example, connecting rod 10 may be machined from a single piece of bar stock.

With reference now to FIGS. 6 to 9, elongate head portion 14 may have a non-circular cross-section. As shown, elongate head portion 14 has a substantially rectangular cross-section having suitable dimensions of, for example, about 6 mm×about 1 mm (0.246 in.×0.039 in.). However, it is envisioned that elongate head portion 14 may have a cross-section that is substantially square, elliptical or any other shape to add rigidity to elongated rounded section 12 of connecting rod 10.

With particular reference back to FIGS. 3, 6 and 7, elongate rounded section 12 of connecting rod 10 is configured and dimensioned to be received in a slot 53 defined in a head portion 52 of bone screw 50, as will be described in detail hereinbelow. While elongate head portion 14 of connecting rod 10 is disposed above elongate rounded section 12, head portion 14 does not appreciably increase the height profile of the screw-rod combination. However, connecting rod 10 affords greater strength and rigidity in comparison with ordinary circular rods with comparable dimensions. As such, connecting rod 10 and bone screw 50 construct affords greater rigidity and strength without increased bulk and profile.

With reference back to FIGS. 2 and 3, screw 50 includes a head portion 52 configured to receive connecting rod 10 therein, a shank 54 extending longitudinally from head portion 52, and a cap 60 releasably coupled to head portion 52 to secure connecting rod 10 within head portion 52. Head portion 52 of bone screw 50 includes a pair of radially opposing walls 56 defining a slot 53 therebetween. Radially opposing walls 56 include internal threads 57 configured for engaging external threads of a set screw (not shown), if needed or desired. Slot 53 defines a U-shape channel configured and dimensioned to receive connecting rod 10. Slot 53 includes a leading end portion 53a (FIG. 2) and a trailing end portion 53b (FIG. 2). In particular, leading end portion 53a has an arcuate configuration configured to accommodate the contour of rounded section 12 of connecting rod 10 for a secure fit therein. Trailing end portion 53b of slot 53 defines a substantially planar surface such that elongate head portion 14 of connecting rod 10 is substantially flush with trailing end portions 56b of the respective walls 56 when connecting rod 10 is positioned within slot 53.

With particular reference now to FIGS. 3 and 4A, the pair of radially opposing walls 56 each includes an engaging portion 58. Engaging portion 58 is disposed adjacent trailing end portion 56b of wall 56. Engaging portions 58 are configured and dimensioned to engage an inner surface 77 (FIG. 4B) of cap 60, as will be described in detail below. Each engaging portion 58 includes a protrusion 59 configured and dimensioned to engage recess 75 (FIG. 4B) defined in cap 60. Recess 75 and protrusion 59 are configured to permit proper alignment and orientation of cap 60 with respect to head portion 52.

With continued reference to FIG. 3, shank 54 includes threads 55 for insertion through vertebral bodies. Bone screw 50 may be made of a biocompatible material such as Titanium (Ti-CP) and its alloys (e.g., Ti-6Al-4V), Cobalt-Chrome Alloy (CoCr), or Stainless Steel (SS). In particular, head portion 52 and shank 54 may be monolithically formed.

With reference now to FIGS. 4A and 4B, cap 60 includes a cover 66 and a pair of opposing arms 68 extending from cover 66. The pair of opposing arms 68 defines a gap therebetween. The gap is dimensioned slightly smaller than an outer diameter of head portion 52 of the bone screw 50, whereby when the pair of opposing arms 68 engages head portion 52 of bone screw 50, cap 60 applies a radially inward force to head portion 52 of bone screw 50 which further secures connecting rod 10 to bone screw 50. Engaging portions 58 of head portion 52 may be chamfered or tapered to facilitate insertion of engaging portion 58 into cap 60.

Cover 66 is substantially planar and the pair of arms 68 is configured to accommodate the radial contour of the respective walls 56 of head portion 52 of bone screw 50. Cap 60 is configured and dimensioned to enclose trailing end portion 56b of head portion 52, such that cover 66 is in planar contact with elongate head portion 14 of connecting rod 10 positioned within slot 53. Cap 60 may be configured to provide, e.g., a snap fit or friction fit, engagement with bone screw 50. In this manner, cap 60 may be releasably attached to head portion 52.

In particular, each arm 68 of cap 60 includes an inner surface 77 that defines recess 75. Recess 75 is configured and dimensioned to engage protrusion 59 extending radially outward from engaging portion 58 of head portion 52. Protrusion 59 and recess 75 are positioned such that when recess 75 and protrusion 59 are properly engaged, proper radial orientation and alignment of cap 60 and head portion 52 are achieved, i.e., walls 56 of head portion 52 and arms 68 of cap 60 are properly aligned to provide proper opening for receipt of connecting rod 10 in slot 53 of head portion 52.

With brief reference back to FIG. 2, when cap 60 is properly secured with head portion 52, elongate rounded section 12 of connecting rod 10 is received in leading end portion 53a of slot 53 having an arcuate configuration and elongate head portion 14 of connecting rod 10 is substantially flush against trailing end portion 56b of head portion 52 of bone screw 50, whereby elongate head portion 14 of connecting rod 10 is in planar contact with cover 66 of cap 60. In this manner, movement of connecting rod 10 within slot 53 is minimized, which in turn reduces inadvertent loosening or detachment of cap 60 from head portion 52. Under such a configuration, connecting rod 10 is positioned securely within slot 53 and is fixed securely with bone screw 50.

With reference now to FIGS. 5A and 5B, it is also envisioned that a cap 160 may include a pair of diametrically opposing protrusions 159 extending radially inward from inner surface 177 of cap 160. The pair of protrusion 159 corresponds to a pair of recesses 175 defined in respective engaging portions 258 of head portion 252 of bone screw 250. In this manner, securement of a cap 160 with head portion 252 of bone screw 250 is achieved.

It is also envisioned that spinal stabilization system 100 may be used with other surgical instruments such as, e.g., a rod reduction device, configured to reduce a rod into position in a rod receiving slot in a head of a bone screw with a controlled, measured action. Reference may be made to U.S. Patent Application Publication Nos. 2009-0018593 and 2011-0087298, the entire contents of each of which are incorporated herein by reference, for a detailed discussion of the construction and operation of a rod reduction device.

With reference now to FIGS. 10-13, spinal stabilization system 100 may further include rod bender devices 80. Rod bender devices 80 each define matching apertures 88 configured to receive and hold at least a portion of connecting rod 10 therein. Rod bender device 80 includes a handle member 82, an elongate body 84 extending distally from handle portion 82, and an engaging portion 86 coupled to elongate body 84. Elongate body 84 is coupled or formed with handle member 82 and engaging portion 86 so as to reduce stress concentration. Handle member 82 may contain scalloped sections to facilitate gripping by the surgeon. Elongate body 84 may have a rectangular cross-section and may define a cavity along the length thereof to reduce the weight of device. Engaging portion 86 defines at least one aperture 88 adapted and dimensioned to receive therethrough connecting rod 10. In particular, inner walls that define aperture 88 are configured to permit insertion of connecting rod 10 through aperture 88 in a single orientation with respect to such aperture.

Figure 10:
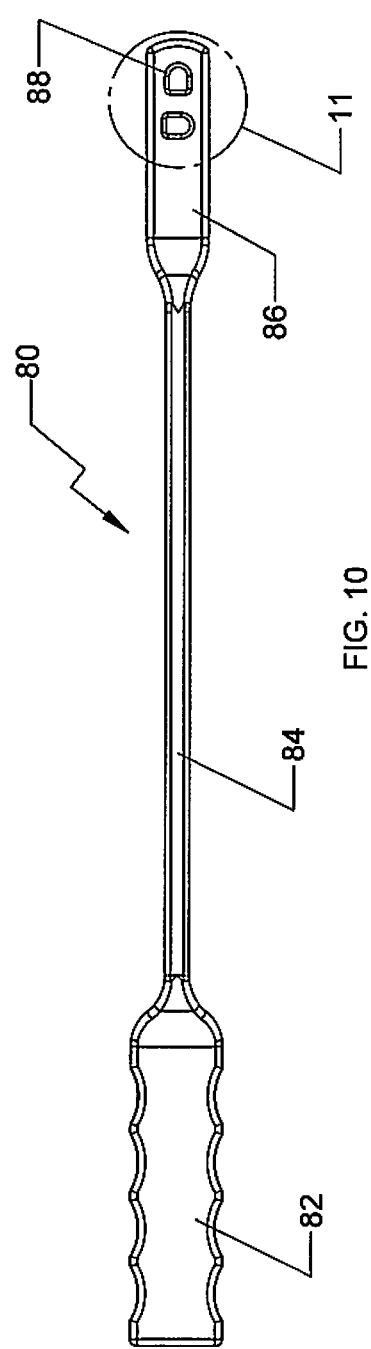
FIG. 10 is a side view of a rod bender device for use with the spinal stabilization system of FIG. 1.
Figure 11:
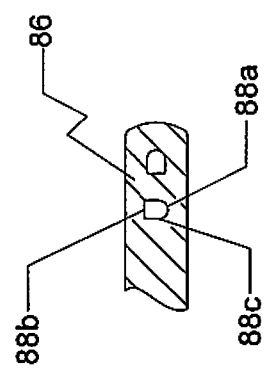
FIG. 11 is a side cross-sectional view of the area of detail indicated in FIG. 10.
Figure 12:
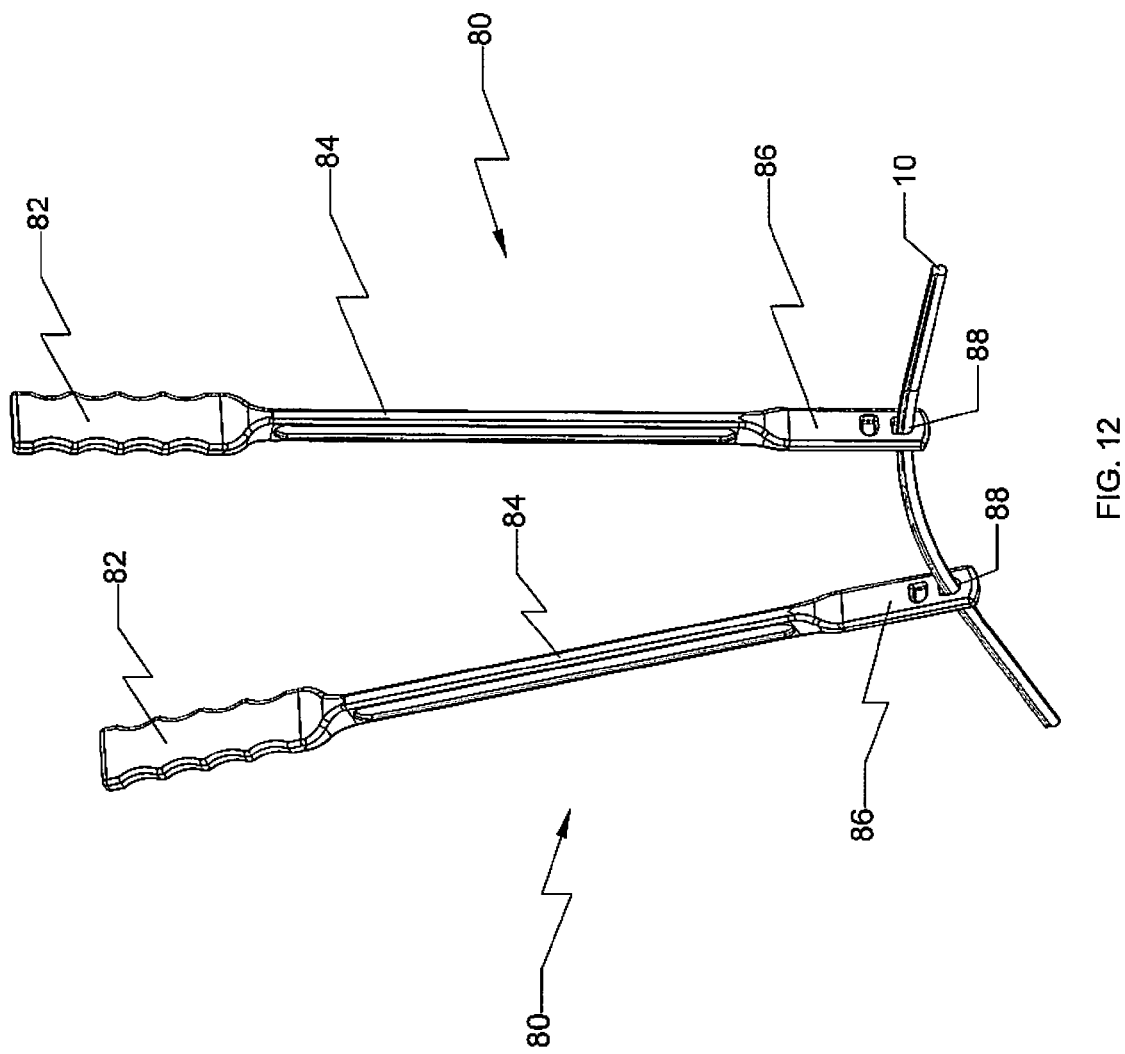
FIG. 12 is a perspective view of a pair of rod bender devices of FIG. 10 having the connecting rod of FIG. 6 inserted therethrough.

Each aperture 88 has an arcuate end wall 88a configured to engage elongate rounded section 12 of connecting rod 10, an opposite substantially straight end wall 88b configured to engage the substantially flat portion of elongate head portion 14 of connecting rod 10, and connecting side walls 88c connecting arcuate end wall 88a and the substantially straight end wall 88b.thus, In this manner, connecting rod 10 is inserted into each aperture 88 in a single orientation. Thus, in order to accommodate insertion of connecting rod in aperture 88 in various orientations, a plurality of apertures 88 are defined in engaging portion 86 in different orientations, as shown in FIGS. 10 and 11. For example, the pair of apertures 88 defined in engaging portion 86 is oriented at a 90-degree angle, whereby the rectangular portions of apertures 88 are orthogonal to each other. In this manner, the surgeon can bend connecting rod 10 in both an anterior-posterior orientation and a medial-lateral orientation. It is also contemplated that connecting rod 10 may be inserted in non-corresponding apertures 88 in rod bender devices 80 to facilitate twisting of connecting rod 10, if necessary or desired.

The length of elongate body 84 may be tailored to meet the needs of the surgical application to provide a suitable long moment arm necessary to provide the surgeon a mechanical advantage to bend connecting rod 10. In addition, it is also envisioned that elongate body 84 may be a hollow tubular member and/or define lightening holes to reduce the weight of device 80.

In use, the surgeon implants a plurality of bone screws 50 in vertebral bodies of a patient. Threaded shank 54 can be driven into the desired vertebral body by providing torsional force via a driving tool (not shown) configured to mate with and grip bone screw 50. After shank 54 is positioned within the vertebral body and the driving tool is removed from bone screw 50, connecting rod 10 is positioned within slot 53 of head portion 52 of bone screw 50.

Spinal stabilization system 100 can be utilized to correct spinal deformity to appropriately contour and shape connecting rod 10 to a desired curvature of the spine, e.g., the sagittal curve. Prior to securing connecting rod 10 with bone screw 50, the surgeon can manipulate and correct the curve of the spinal column, i.e., to manually manipulate and reduce the "rib hump." After placing the spine in proper position, the surgeon can bend connecting rod 10 prior to securing connecting rod 10 to the first two points of the spinal column where the construct is to be attached.

The surgeon can bend connecting rod 10 by utilizing the pair of rod bender devices 80. In use, connecting rod 10 is inserted through apertures 88 of rod bender devices 80 and force is applied at handle members 82 of rod bender devices 80 to appropriately contour and shape connecting rod 10 to a desired curve.

At this time, connecting rod 10 is positioned in respective slots 53 of bone screws 50 implanted in vertebral bodies. The user can now position caps 60 in respective heads 52 to securely fix connecting rod 10 with bone screws 50.

The rod and bone screw combination of the present disclosure may provide particular advantages in scoliosis or other spinal deformity surgery in which high stress levels are exerted upon such constructs at particular levels in the construct or over the entire length of such a construct.

Although the illustrative embodiments of the present disclosure have been described herein with reference to the accompanying drawings, the above description, disclosure, and figures should not be construed as limiting, but merely as exemplifications of particular embodiments. For example, it is contemplated that in certain applications, a set screw (not shown) may be used with some of bone screws 50, while other bone screws 50 utilize cap 60 to secure connecting rod 10 with bone screw 50. As briefly discussed hereinabove, threads on a set screw may engage internal threads 57 of opposing walls 56 to secure connecting rod 10 with bone screw 50. One skilled in the art will recognize that the present disclosure is not limited to use in spine surgery, and that the instrument and methods can be adapted for use with any suitable surgical device. It is to be understood, therefore, that the disclosure is not limited to those precise embodiments, and that various other changes and modifications may be effected therein by one skilled in the art without departing from the scope or spirit of the disclosure.

What is claimed is:

1. A spinal stabilization system comprising:
   a connecting rod including an elongate rounded section, an elongate head portion, and a neck portion connecting the elongate rounded section with the elongate head portion; and
   a bone screw including a head portion defining a slot, a shank extending longitudinally from the head portion, and a cap configured to secure the connecting rod in the slot, the head portion including a protrusion extending radially outward from an outer surface of the head portion, the cap including a cover and a pair of opposing arms extending from the cover, the pair of opposing arms defining a gap therebetween, the gap dimensioned to receive at least a portion of the head portion of the bone screw therein, at least one arm of the pair of opposing arms including an inner surface defining a recess configured to receive the protrusion of the head portion to secure the cap on the head portion, the protrusion and the recess having complementary configurations, the slot including a leading end portion configured to receive the elongate rounded section of the connecting rod, wherein a trailing end of the head portion of the bone screw is flush with a trailing surface of the elongate head portion of the connecting rod when the connecting rod is disposed in the slot.

2. The spinal stabilization system according to claim 1, wherein the leading end portion of the slot has an arcuate configuration dimensioned to accommodate the elongate rounded section of the connecting rod.

3. The spinal stabilization system according to claim 1, wherein the cover of the cap is in planar contact with the elongate head portion of the connecting rod when the connecting rod is secured in the slot.

4. The spinal stabilization system according to claim 3, wherein the head portion of the bone screw includes a pair of radially opposing walls defining the slot therebetween, the pair of radially opposing walls securely engaging the pair of opposing arms of the cap.

5. The spinal stabilization system according to claim 4, wherein the pair of radially opposing walls of the head portion of the bone screw includes internal threads.

6. The spinal stabilization system according to claim 3, wherein the neck portion of the connecting rod is narrower than the elongate rounded section of the connecting rod.

7. The spinal stabilization system according to claim 1, wherein a width of the elongate head portion of the connecting rod is substantially identical to a radius of the slot.

8. The spinal stabilization system according to claim 1, wherein the cap is releasably attached to the head portion of the bone screw.

9. The spinal stabilization system according to claim 1, wherein the cap is attached to the head portion of the bone screw by a friction fit or a snap fit.

10. The spinal stabilization system according to claim 1, wherein the shank of the bone screw includes threads.

11. The spinal stabilization system according to claim 1, wherein the cap and the head portion of the bone screw are made of the same material.

12. The spinal stabilization system according to claim 11, wherein the cap is made of titanium or titanium alloy.

13. The spinal stabilization system according to claim 1, wherein the gap is smaller than an outer diameter of the head portion of the bone screw.

14. The spinal stabilization system according to claim 1, wherein the elongate head portion of the connecting rod includes a non-circular cross-section.

15. The spinal stabilization system according to claim 14, wherein the elongate head portion of the connecting rod includes a rectangular cross-section.

16. A spinal stabilization system comprising:
   a connecting rod including an elongate rounded section, an elongate head portion, and a neck portion connecting the elongate rounded section with the elongate head portion; and
   a bone screw including a head portion defining a slot, a shank extending longitudinally from the head portion, and a cap configured to secure the connecting rod in the slot, the cap defining a gap dimensioned to receive at least a portion of the head portion of the bone screw therein, wherein the head portion includes a protrusion member extending radially outward from an outer surface of the head portion, the cap including an inner surface defining a recess configured and dimensioned to engage the protrusion member of the head portion such that the cap inhibits rotation of the connecting rod when the connecting rod is disposed in the slot of the head portion.

17. A spinal stabilization system comprising:
a connecting rod including an elongate rounded section, an elongate head portion, and a neck portion connecting the elongate rounded section with the elongate head portion; and
a bone screw including a head portion defining a slot, a shank extending longitudinally from the head portion, and a cap configured to secure the connecting rod in the slot, wherein the head portion includes an outer surface defining a recess, the cap including an inner surface including a protrusion extending radially inward, the protrusion and the recess having complementary configurations to inhibit rotation of the cap relative to the head portion when the protrusion engages the recess to secure the cap on the head portion, wherein a trailing surface of the elongate head portion of the connecting rod is coplanar with a trailing end portion of the bone screw when the connecting rod is disposed in the slot.

* * * * *